(12) United States Patent
Stashenko et al.

(10) Patent No.: US 11,028,338 B2
(45) Date of Patent: Jun. 8, 2021

(54) **METHOD FOR MAKING FULL USE OF *LIPPIA ORIGANOIDES***

(71) Applicant: UNIVERSIDAD INDUSTRIAL DE SANTANDER, Bogota (CO)

(72) Inventors: Elena Stashenko, Bogota (CO); Diego Camilo Duran Garcia, Bogota (CO); Jairo Rene Martinez Morales, Bogota (CO); Yuri Cordoba Campo, Bogota (CO); Anderson Julian Arias Velandia, Bogota (CO); Jesica Julieth Mejia Medina, Bogota (CO); Camilo Andres Tavera Reyes, Bogota (CO)

(73) Assignee: UNIVERSIDAD INDUSTRIAL DE SANTANDER, Bogota (CO)

( * ) Notice: Subject to any disclaimer, the term of this patent is extended or adjusted under 35 U.S.C. 154(b) by 43 days.

(21) Appl. No.: 16/474,470

(22) PCT Filed: Dec. 13, 2017

(86) PCT No.: PCT/IB2017/057862
§ 371 (c)(1),
(2) Date: Jun. 27, 2019

(87) PCT Pub. No.: WO2018/122654
PCT Pub. Date: Jul. 5, 2018

(65) Prior Publication Data
US 2019/0345412 A1    Nov. 14, 2019

(30) Foreign Application Priority Data

Dec. 27, 2016  (CO) .................. NC2016/0005880

(51) Int. Cl.
*C11B 9/02* (2006.01)
*A23L 33/105* (2016.01)
*A01N 65/08* (2009.01)
*A61K 8/34* (2006.01)
*A61K 8/49* (2006.01)
(Continued)

(52) U.S. Cl.
CPC .............. *C11B 9/025* (2013.01); *A01N 65/08* (2013.01); *A23L 33/105* (2016.08); *A61K 8/347* (2013.01); *A61K 8/498* (2013.01); *A61K 8/602* (2013.01); *A61K 31/05* (2013.01); *B01D 3/38* (2013.01); *B01D 11/0203* (2013.01); *B01D 11/0288* (2013.01); *B01D 11/0296* (2013.01); *C05F 11/00* (2013.01); *C07C 7/04* (2013.01); *C07C 7/10* (2013.01); *C10L 5/44* (2013.01); *A23V 2002/00* (2013.01); *C10L 2200/0469* (2013.01)

(58) Field of Classification Search
CPC ... C11B 9/02; C11B 9/022; C10L 5/44; C07C 7/04; C07C 7/10; B01D 11/02; B01D 3/38
See application file for complete search history.

(56) References Cited

PUBLICATIONS

Carreno (Wild oregano (*Lippia origanoides*) Alto Patía: Effect of the method of obtaining extracts on the composition and antioxidant activity of the same, 2012, Universidad Nacional de Colombia—Sede Bogotá) (Year: 2012).*

(Continued)

*Primary Examiner* — Youngsul Jeong
(74) *Attorney, Agent, or Firm* — Hoglund & Pamias, PSC; Roberto J. Rios

(57) ABSTRACT

The present invention relates to a method for extracting, separating and purifying compounds of interest obtained from essential oils and plant extracts which is continuously held.

12 Claims, 1 Drawing Sheet

(51) Int. Cl.

| | |
|---|---|
| *A61K 8/60* | (2006.01) |
| *A61K 31/05* | (2006.01) |
| *B01D 3/38* | (2006.01) |
| *B01D 11/02* | (2006.01) |
| *C05F 11/00* | (2006.01) |
| *C07C 7/04* | (2006.01) |
| *C07C 7/10* | (2006.01) |
| *C10L 5/44* | (2006.01) |

(56) References Cited

PUBLICATIONS

Stashenko et al. (Composition and Antioxidant activity of Essential Oils of Lippia origanoides H.B.K. grown in Colombia, 2008, Natural Product Communications, vol. 3, No. 4, p. 5630566) (Year: 2008).*

Oliveira et al. (Chemical and antimicrobial analyses of essential oil of Lippia origanoides H.B.K., 2007, Food Chemistry, vol. 101, pp. 236-240) (Year: 2007).*

Teixeira et al. (Essential Oils from Lippia origanoides Kunth. and Mentha spicata L.: Chemical Composition, Insecticidal and Antioxidant Activities, 2014, American Journal of Plant Sciences, vol. 5, pp. 1181-1190) (Year: 2014).*

Oman et al. (Application of supercritical fluid extraction for the separation of nutraceuticals and other phytochemicals from plant materials, Macedonian Journal of Chemistry and Chemical Engineering, 2013, vol. 32, No. 2, pp. 183-226) (Year: 2013).*

* cited by examiner

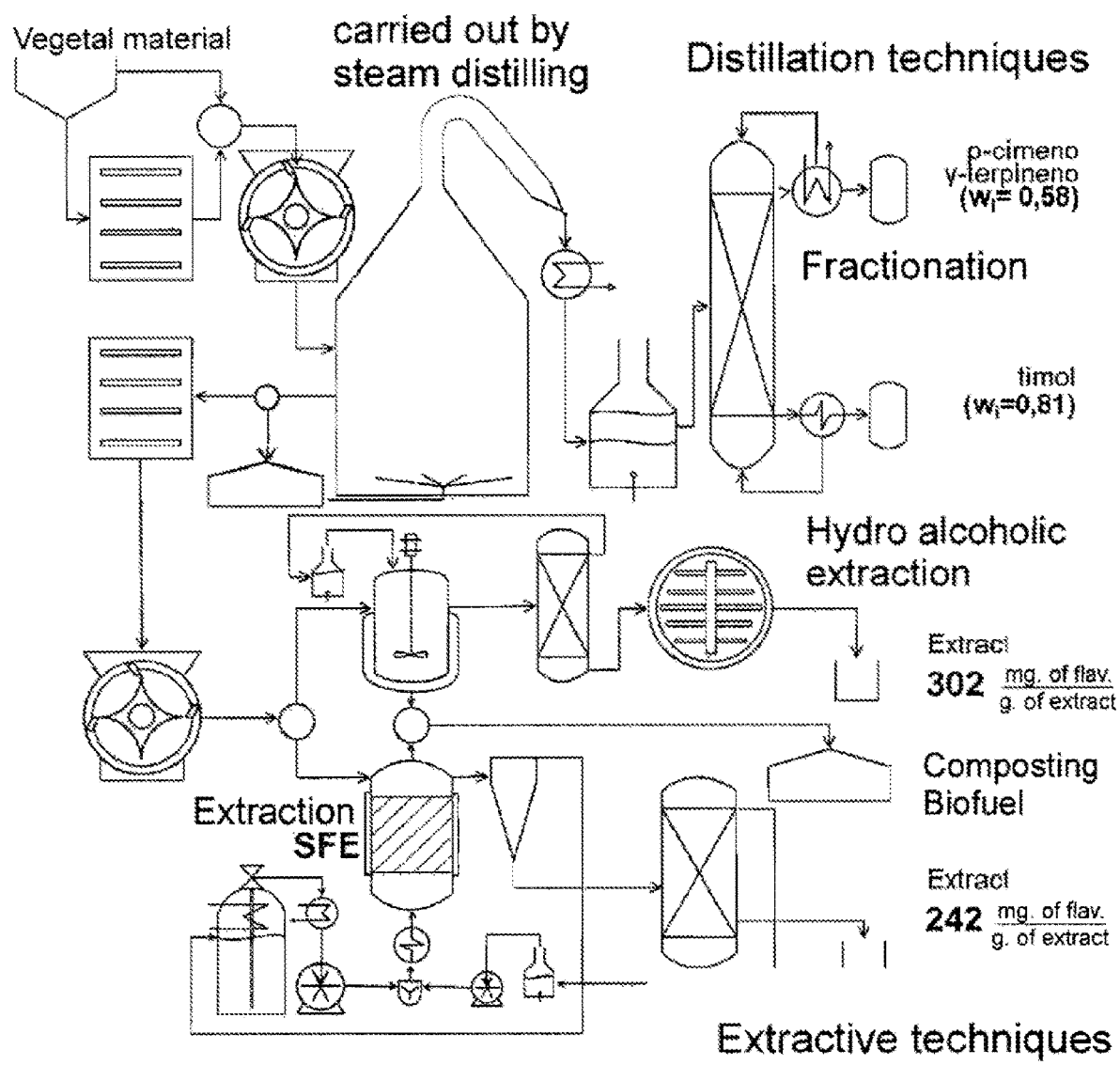

METHOD FOR MAKING FULL USE OF *LIPPIA ORIGANOIDES*

FIELD OF INVENTION

The present invention relates to a method for extracting, separating and purifying compounds of interest obtained from essential oils and plant extracts.

BACKGROUND OF INVENTION

Plants are a source of a great quantity of compounds with multiple uses at industrial level. Industries of cosmetics, food, drugs and livestock, agricultural, veterinary among others, benefit from the great quantity of compounds obtained from plants. Therefore, from immemorial time, different processes for extracting and purifying compounds from plants have been developed. Most of these processes consist in unit independent operations that isolate molecules of interest in a separated manner. Processes not always reach the efficient separation and purification of valuable compounds from a same matrix, since to obtain a compound of particular interest, in some cases, others are degraded.

Since it is very important for the above-mentioned industries to take full advantage of the raw material to obtain the most and better product, it is necessary to develop continuous industrial processes allowing integrally using plants, to carry out their extraction depending on families of compounds to be extracted.

A plant with a very particular interest, due to its yield and variety of compounds that can be obtained and used by several industries is the *Lippia origanoides*. The present invention solves the integral use of the *Lippia origanoides* as a raw material to obtain natural products used by different industries (cosmetics, food, drugs, agricultural, veterinary, among others).

SUMMARY OF THE INVENTION

The present invention relates to the design of a process for extracting, separating and purifying compounds of interest present in the *Lippia origanoides*. The configuration of unit operations, corresponding to green methods of distillation and extraction described in the process, according to the present invention, provide a high added value to products by means of the possibility of concentrate three families of molecules of interest: light essential oil fraction composed of phenylpropanes precursors, fraction composed of phenylpropanes with biological activity and extract fraction composed of flavonoids.

Process is addressed to isolate the most valuable compounds such as thymol, carvacrol, p-cymene, gamma terpinene, pinocembrin and naringenin of the plant, to obtain products with concentrations of the compound's family ranging among 80 and 99%. The way of development allows obtaining quantities of phenylpropanes and flavonoids present in the plant per unit of measure of raw material. All the residues from the plant because of the extraction stages are used as by-products or reused in the process.

Therefore, it is the purpose of the present invention, to provide a process where fractionation in situ exists. It is also a purpose of the present invention, to provide a process where this fractionation is carried out during the distillation stage. It is also a purpose of the present invention, to provide elements of decision to determine whether the initial extraction of the plant material must be carried out by steam distilling or hydrodistillation.

The process according to the present invention allows obtaining extracts and essential oils from *Lippia origanoides* with greater added value because it allows concentrating the most valuable compounds present in the plant, such as phenylpropanes thymol and carvacrol, its precursors p-cymene and gamma—terpinene, as well as flavonoids.

Finally, it is a purpose of the present invention to provide an integral process for the use of *Lippia origanoides* which reuses the residual biomass of the plant in the same process of obtaining essential oils and extracts.

BRIEF DESCRIPTION OF THE DRAWINGS

The FIGURE shows a schematic diagram of the process according to the present invention.

DETAILED DESCRIPTION OF THE INVENTION

According to the above, the process of this invention is addressed to isolate the most valuable components such as thymol, carvacrol, p-cymene, gamma-terpinene, pinocembrin and naringenin from the plant, to obtain products of concentration ranging among 80 and 99%. The way in which the development is arranged allows obtaining greater quantities of phenylpropanes and flavonoids present in the plant per unit of measure of the raw material. All residues from the plant because of the extraction stages are used as by-products or are reused in the process.

The process of extraction of natural products from *Lippia origanoides* according to the present invention, is focused on increasing the added value of the oil and extract of the plant. The phenylpropanoids thymol and carvacrol along with their biosynthetic precursors p-cymene and gamma-terpinene in addition to the flavonoids pinocembrin and naringenin, among others, are compounds with great bioactivity that are isolated by means of the present development.

The process begins with the entry of the plant material of *Lippia origanoides* with known humidity. According to the humidity and the interest of the products of the process, it is decided whether the raw material should be dried or not. The fresh or dry plant material is subjected to a reduction treatment of particle size. The determined values of particle size are between 0.5 and 5 cm.

The plant material with reduced particle size is charged to a distillation equipment, where the separation of the essential oil takes place. The distillation process can be made by steam distilling or hydro distillation, two known methodologies for obtaining essential oils.

The loading density of the plant material in the distillation equipment is between 200 and 320 kg/m3. When the distillation method is by steam the steam pressure of the boiler and the steam flow is 50-110 psi 0.8-1.5 L/min. With the distillation method by hydrodistillation the amount of heat supplied to the system must be the necessary to maintain the steam flow between 0.8 and 1 L/min. The distillation process is carried out between 60 and 150 minutes, depending on the amount of oil of the matrix. The oil mixed with condensed water is fractioned in time, the oil collected in the first 10-20 minutes corresponds to the light fraction. This fraction corresponds to the most volatile product enriched with precursors of phenylpropanes such as p-cymene and gamma-terpinene. (wi=0.5-0.6). After collecting the light fraction, the essential oil obtained from the distiller corresponds to the heavy fraction, a mixture with a higher content of phenylpropanes thiol and carvacrol than the so-called light fraction. The same methodology is used when the process is performed by hydrodistillation, increasing the time of collection up to 30 minutes.

The oil is separated from the hydrolat in a decanter or communicating vessels system. The hydrolat, which is a very aromatic mixture of molecules present in the *Lippia origanoides* that dissolved in the water, is reused in the distillation process and then recovered as a by-product. Once the essential oil corresponding to the heavy fraction is decanted, it is introduced to a fractionated distillation column where the phenylpropanes are concentrated at mass fractions (wi=0.8-1) at the bottom of the column. The condensates obtained in this stage of fractional distillation are collected at the top of the column and are rich in p-cymene and gamma-terpinene precursors.

For such reason, this product is mixed with the volatile fraction obtained in the first 10-30 minutes of distillation by steam or hydrodistillation, as the case may be. If the concentration of phenylpropanes present in the oil is greater than 75% the fractional process is not carried out, instead a process of slow crystallization under −15° C. is made which by the gradual decreasing of temperature and addition of a thymol or carvacrol crystal depending on the chemotype, the mass fraction of the phenylpropane is concentrated over 9.9.

The distilled plant material is again dried and extracted by two different techniques: hydroalcoholic extraction and extraction with supercritical carbon dioxide, depending on the type of flavonoid required, whether glycosidated or not. With these known techniques, flavonoid concentrations of 300-320 and 240-260 mg of flavonoids are obtained per gram of extract respectively.

The supercritical extract enriched with flavonoids of 300-320 mg of flavonoids per gram and 240-260 mg of flavonoids per gram is obtained in the extractive stage corresponding to the supercritical extraction process, once the plant material has already been distilled. This technique differs from the distillation in that a solvent that solubilizes the extract is not used. This product is viscous and not liquid or volatile such as the volatile fraction enriched with p-cymene and gamma-terpinene precursors or the heavy fraction enriched with phenylpropanoids thymol and carvacrol.

All the design parameters such as flows, pressures, temperature of each stage of the process are optimized depending on the plant conditions.

Products and byproducts of the process with their applications are described in the following table:

TABLE 1

Products and by-products obtained from the integral use of *Lippia origanoides*.

| | Description | Use |
| --- | --- | --- |
| Products | Volatile fraction enriched with p-cymene and gamma-terpinene precursors. ($w_i$ = 0.5-0.6) | Perfumery input, contribution of citric notes. |
| | Heavy fraction enriched with phenylpropanoids thymol and carvacrol ($w_i$ = 0.8-1) | Input for the cosmetic and personal hygiene industry (mouthwash, soaps). Input for the food industry. Input for the pharmaceutical industry. Input for animal growth promoters (poultry, pigs, others) |
| | Hydroalcoholic extract enriched with glycosidic flavonoids 300-320 mg flav/g | Input of the cosmetic and food industry as a stable antioxidant |
| | Supercritical extract enriched with flavonoids | Input of the cosmetic and food industry as a less stable antioxidant |
| Sub-products | 240-260 mg flav/g Hydrolat | Recirculation in the hydrodistillation process. Base for the air freshener industry. Biorepellents and agricultural biopesticides. |
| | Residual biomass | Reuse in the process as a biofuel or as composted fertilizer for crops of the same plant or others |

Although a description of one of the preferred embodiments of the invention has been made, it is not limiting since the invention is limited only by the following claims. An expert skilled in the art will understand that it is possible to make changes and modifications to the process described in the present application. This can also be modified in its conditions or stages without leaving the spirit of the invention.

The invention claimed is:

1. A process for extracting compounds of interest from *Lippia origanoides* plants comprising the steps of:
   step a) reducing a plant material of *Lippia origanoides* plant to a particle size between 0.5 cm and 5 cm;
   step b) loading the reduced plant material from step a) into a distillation equipment;
   step c) subjecting the loaded plant material from step b) to a first distillation thereby producing distillates;
   step d) separating said distillates into a light fraction and a heavy fraction;
   step e) drying a residue of the distilled plant material from step c); and
   step f) subjecting said dried residue from step e) to an extraction with solvents to recover other compounds;
   wherein the process is performed continuously.

2. The process according to claim 1, wherein the first distillation of step c) is conducted by a steam distilling process.

3. The process according to claim 1, wherein the first distillation of step c) is conducted by a hydrodistillation process.

4. The process according to claim 1, wherein a light fraction mixed with water is separated during the first 10-30 minutes of step c).

5. The process according to claim 4, wherein the light fraction mixed with water comprises a volatile fraction enriched with phenylpropanes p-cymene and gamma-terpinene precursors.

6. The process according to claim 4, wherein the light fraction obtained in step d) is combined with the light fraction mixed with water separated from step c).

7. The process according to claim 1, wherein said heavy fraction is loaded into a fractionating column.

8. The process according to claim 1, wherein said heavy fraction is subjected to a crystallization process.

9. The process according to claim 1, wherein step f) is conducted with a hydro alcoholic mixture.

10. The process according to claim 1, wherein step f) is conducted with supercritical carbon dioxide and ethanol.

11. The process according to claim 1, wherein a hydrolate obtained in step c) is recirculated during the first distillation process of step c), and at the end of said first distillation process of step c) any hydrolate left is collected as a by-product used to manufacture air fresheners, biopesticides, or repellents.

12. The process according to claim 1, wherein a residual of said dried plant material obtained from extraction in step f) is used as a by-product for composting or as biofuel used as a source of energy for the process.

\* \* \* \* \*